United States Patent
Thuesen et al.

(10) Patent No.: US 11,234,897 B2
(45) Date of Patent: Feb. 1, 2022

(54) PACKAGED MULTI-DOSE LIQUID DEXTROMETHORPHAN HYDROBROMIDE FORMULATION

(71) Applicant: DXM Pharmaceutical, Inc., Katy, TX (US)

(72) Inventors: Mark Lawrence Thuesen, Katy, TX (US); Steve Shane Sanders, Lake Charles, LA (US); Steve J. Bannister, Tampa, FL (US)

(73) Assignee: DXM Pharmaceutical, Inc., Katy, TX (US)

( * ) Notice: Subject to any disclaimer, the term of this patent is extended or adjusted under 35 U.S.C. 154(b) by 0 days.

(21) Appl. No.: 15/936,129

(22) Filed: Mar. 26, 2018

(65) Prior Publication Data

US 2018/0271746 A1    Sep. 27, 2018

Related U.S. Application Data

(60) Provisional application No. 62/606,153, filed on Jan. 26, 2018, provisional application No. 62/476,921, filed on Mar. 27, 2017.

(51) Int. Cl.

| | | |
|---|---|---|
| *A61K 9/08* | (2006.01) | |
| *A61K 31/485* | (2006.01) | |
| *A61P 11/14* | (2006.01) | |
| *A61J 1/05* | (2006.01) | |
| *A61J 7/00* | (2006.01) | |
| *A61K 9/00* | (2006.01) | |
| *A61K 47/26* | (2006.01) | |
| *A61J 1/06* | (2006.01) | |

(52) U.S. Cl.
CPC ............... *A61J 1/05* (2013.01); *A61J 7/0046* (2013.01); *A61K 9/0095* (2013.01); *A61K 31/485* (2013.01); *A61P 11/14* (2018.01); *A61J 1/06* (2013.01); *A61J 2205/30* (2013.01); *A61K 47/26* (2013.01)

(58) Field of Classification Search
None
See application file for complete search history.

(56) References Cited

U.S. PATENT DOCUMENTS

| | | |
|---|---|---|
| 2,676,177 A | 4/1954 | Schnider et al. |
| 2,784,456 A | 3/1957 | Grabenstein |
| 3,879,511 A | 4/1975 | Goodhart et al. |
| 4,127,221 A | 11/1978 | Vere |
| 4,747,618 A | 5/1988 | Instance |
| 4,996,291 A | 2/1991 | Yoshinaka et al. |
| 5,154,926 A | 10/1992 | Kawasaki et al. |
| 5,316,161 A | 5/1994 | Gargione |
| 5,330,081 A | 7/1994 | Davenport |
| 5,616,621 A | 4/1997 | Popli et al. |
| 5,658,919 A | 8/1997 | Ratnaraj et al. |
| 5,730,997 A | 3/1998 | Lienhop et al. |
| 5,763,449 A | 6/1998 | Anaebonam et al. |
| 5,860,238 A | 1/1999 | Anderson |
| 5,866,585 A | 2/1999 | Fogel |
| 5,922,773 A | 7/1999 | Lipton et al. |
| 5,962,461 A | 10/1999 | Anaebonam et al. |
| 6,025,369 A | 2/2000 | Rosenquist et al. |
| 6,054,128 A | 4/2000 | Wakat |
| 6,231,958 B1 | 5/2001 | Kim et al. |
| 6,337,083 B1 | 1/2002 | Fuisz |
| 6,583,152 B2 | 6/2003 | Sosnowski et al. |
| 6,846,495 B2 * | 1/2005 | Dobrozsi ............. A61K 9/0056 424/439 |
| 7,101,572 B2 | 9/2006 | Santos et al. |
| 8,017,623 B2 | 9/2011 | Singh |
| 8,137,709 B1 | 3/2012 | Volden |
| 8,273,434 B2 | 9/2012 | Zietlow et al. |
| 9,283,363 B1 | 3/2016 | Scorzellit et al. |
| 9,382,049 B2 | 7/2016 | Kershner et al. |
| 9,498,435 B2 | 11/2016 | Allio et al. |
| 2006/0121066 A1 * | 6/2006 | Jaeger ................ A61K 31/7012 424/400 |

(Continued)

FOREIGN PATENT DOCUMENTS

| | | |
|---|---|---|
| WO | 00/41692 A2 | 7/2000 |
| WO | 00/41694 A2 | 7/2000 |

(Continued)

OTHER PUBLICATIONS

Merriam-Webster's Collegiate Dictionary, 11th ed., entry for "aqueous," p. 62. (Year: 2004).*
Rowe; "Handbook of Pharmaceutical Excipients, 6th ed.," entry for "Propylene Glycol" pp. 592-593. (Year: 2009).*
Ansel et al.; "Pharmaceutical Dosage Forms and Drug Delivery Systems," 7th ed., Chapter 12, Solutions, pp. 296-345. (Year: 1999).*
Sweetman ("Martindale, The complete drug reference," 33rd ed., pp. 1082-1102. (Year: 2002).*

(Continued)

*Primary Examiner* — Tigabu Kassa
*Assistant Examiner* — Ivan A Greene
(74) *Attorney, Agent, or Firm* — Keith B. Willhelm

(57) ABSTRACT

Multi-dose packaged over-the-counter antitussive syrups comprise a bottle containing about 75 ml or less of a liquid formulation of dextromethorphan hydrobromide. The liquid formulation provides at least two doses of dextromethorphan hydrobromide. Multi-dose packaged over-the-counter liquid formulations comprise a bottle having a capacity of about 100 ml or less, at least two doses of the liquid formulation carried within the bottle, a cap, a dosage cup releasably carried on the cap and a shrink wrap substantially enveloping the bottle and the dosage cup. Antitussive syrups comprise water, dextromethorphan hydrobromide in amounts from about 6 to about 25 mg/ml, and sweetener in amounts from about 200 to about 800 mg/ml.

11 Claims, 3 Drawing Sheets

(56) References Cited

U.S. PATENT DOCUMENTS

| | | | |
|---|---|---|---|
| 2008/0085892 A1* | 4/2008 | Kandeepan | A61K 31/075 514/226.5 |
| 2015/0056288 A1* | 2/2015 | Dubey | A61K 31/4402 424/490 |
| 2018/0092837 A1 | 4/2018 | Nutalapati et al. | |

FOREIGN PATENT DOCUMENTS

| | | |
|---|---|---|
| WO | 03/011306 A1 | 2/2003 |
| WO | 2013/088271 A1 | 6/2013 |

OTHER PUBLICATIONS

The Merck Index Online entry for "Dextromethorphan," Monograph ID M4227, pp. 1-2. (Year: 2013).*
Australian Patent Office, International Search Report (PCT/US2018/024366) (dated Jun. 4, 2018).
Australian Patent Office, Written Opinion of the Int'l Searching Authority (PCT/US2018/024366) (dated Jun. 4, 2018).
Miscellaneous Photos of OTC Formulations.
European Patent Office, Invitation to Pay Additional Fees and, Where Applicable, Protest Fee (PCT/US2020/036734) (Oct. 6, 2020).

* cited by examiner

PACKAGED MULTI-DOSE LIQUID DEXTROMETHORPHAN HYDROBROMIDE FORMULATION

FIELD OF THE INVENTION

The present invention relates to packaged over-the-counter liquid drug formulations, and more particularly, to such formulations and multi-dose delivery systems for such formulations.

BACKGROUND OF THE INVENTION

Over-the-counter ("OTC") drugs are sold directly to consumers and do not require a prescription from a healthcare professional. They are generally recognized as safe and effective for their intended uses and allow consumers to self-diagnose and treat a variety of conditions. OTC drugs are available in many different forms. Common forms include topicals, such as creams and ointment which are intended to be applied to the skin, and orals, such as pills and liquids that are taken by mouth. They may be used to treat many different conditions. Most commonly, they are sold to relieve aches and pains, to relieve fever, congestion, coughing and other cold and flu symptoms, to relieve allergic reactions, and to relieve gas, acid reflux, and other gastrointestinal symptoms.

OTC drugs are a large market. Global sales of over-the-counter ("OTC") drugs likely exceed $60 billion per year. The market in the United States represents over 30% of the worldwide market with approximately $20 billion in annual sales. The largest portion of that—approximately $7 billion—represents sales of cough and cold OTC drugs. The consensus is that such sales will continue to expand significantly, especially in developing markets.

Despite an expanding market, however, competition in the OTC market is fierce. Hundreds, if not thousands of new OTC drugs are introduced every year. Unlike new drugs, OTC drugs typically do not require any individual review by regulatory agencies and may be introduced more quickly and with less expense. In the United States, for example, the United States Food and Drug Administration ("FDA") has established "monographs" covering over 200 different active ingredients classified into 26 therapeutic categories. The monographs are essentially rule books. They specify acceptable active ingredients, uses or "indications," doses, formulations, testing, and labeling requirements that are intended to ensure that an OTC drug is marketed properly. If an OTC drug meets the standards in a monograph and complies with other applicable FDA regulations, the drug will be considered safe and effective and may be marketed without a lengthy and costly individual review.

Dextromethorphan (3-methoxy-N-methylmorphinan) is one of the most widely used cough suppressant or antitussive agent. Dextromethorphan (DXM) and dextromethorphan hydrobromide (DXM HBr) are approved active ingredients for antitussive OTC drugs and are covered by an FDA final monograph. They are available, either alone or in combination with other active ingredients, in more than 125 OTC formulations, primarily in the form of pills or liquids to be taken orally. The most common active ingredients with which they are combined include analgesics such as acetaminophen, antihistamines such as brompheniramine, chlorpheniramine, and diphenhydramine, decongestants such as pseudoephedrine, and expectorants such as guaifenesin. Whether alone or formulated with other active ingredients, DXM and DXM HBr OTC formulations are almost exclusively distributed in multi-dose packages.

Dextromethorphan and dextromethorphan hydrobromide, like many OTC active ingredients, have a bitter taste. That bitterness can make consumers hesitant to follow recommended dosages. It also can cause consumers to prefer less bitter formulations. Thus, OTC formulations with DXM and DXM HBr typically include flavoring agents or agents designed to mask the bitterness. Various other approaches, such as increasing the viscosity of the formulation also are known to reduce the level of perceived bitterness. High doses of DXM also are known to cause nausea and vomiting in some people. Antienemic agents which can minimize such side effects, however, are not approved for use in combination with DXM or DXM HBr. The primary method of avoiding both the bitter taste of and possible nausea and vomiting, however, is to formulate the syrup with relatively low concentrations of DXM or DXM HBr.

There are many challenges in marketing and distributing an OTC drug. Manufacturers are increasingly called upon to package and promote their products to meet ever more particularized consumer and retail demands. Such customization may take many different forms. A manufacturer may be required, for example, to provide an OTC drug in both pill and liquid form, in different strengths, in various combinations with other OTC drugs, in multiple package sizes and formats, in adult and child formulations, and even in different flavors and "sugar-free." Pfizer, for example, currently markets 20 different Robitussin® liquid cough and cold formulations all in various sizes.

Even under the best of circumstances it is difficult for an OTC product to find room on a retailer's shelf. Retailers may be more than willing to provide their customers with a variety of choices, but shelf space is limited. Products often are displayed within inches of each other on store shelves, and there is little or no cost for a consumer to switch brands. A relatively few brands, such as Robitussin and Mucinex, have built a loyal base of consumers, but most brands fight daily for their survival. Even famous, established brands face challenges from knock-offs and store brands and must be vigilant in protecting their market share.

Consequently, most OTC drug brands are distributed through relatively large retailers, such as drugstores and grocery stores. A typical drugstore may have about 11,000 square feet (sf) of retail space. An average grocery store may have about 45,000 sf, with superstores having up to about 200,000 sf. While such stores sell a large number of SKUs (Stock Keeping Units) in many different product categories, they still devote relatively large amounts of shelving to OTC drug formulations. A typical drug store, for example, may have 100 to 150 feet of shelf space devoted to cough, cold, and flu formulations alone. Even with relatively large sections, however, even a famous brand like Robitussin may only be able to display half of its formulations in a couple of sizes. Most OTC drug brands, even famous brands, have not been able to successfully distribute their products through convenience stores and other small retail outlets.

Although there now are smaller "kiosk" and larger "hyper" convenience stores, traditional convenience stores have been in the range of 2,400 to 2,500 square feet. They not only stock many fewer SKUs, but much of their space is devoted to the products where they derive their greatest sales. Excluding gas, the top product categories are lottery tickets, cigarettes, non-alcoholic packaged beverages, food service, beer, tobacco products other than cigarettes, candy, salty snacks, general merchandise, fluid milk products, and packaged sweet snacks. Those top categories account for the vast majority of sales in convenience stores, with the top five categories accounting for approximately 80% of sales.

There is very little space left for OTC drugs and other products. A "well stocked" convenience store will average less than 5 feet of shelf space stocking 20 to 30 SKUs of OTC drugs. Most of those SKUs are typically pills as many doses of OTC pills may be provided in relatively small packaging. Multi-dose liquid OTC drugs typically require much larger packaging. Fewer multi-dose liquid OTC drug SKUs may be displayed in the same shelf space. Consequently, some OTC manufacturers have provided single dose packaging for liquid OTC drugs. Such packaging necessarily can be much smaller. Nevertheless, the bulky packaging required for multi-dose liquid OTC drugs has made it difficult for manufacturers to distribute through convenience stores. At most, a convenience store may limit its inventory to 2 to 5 multi-dose liquid OTC formulations. Some convenience stores stock pill and tablet OTC drugs exclusively.

The statements in this section are intended to provide background information related to the invention disclosed and claimed herein. Such information may or may not constitute prior art. It will be appreciated from the foregoing, however, that there remains a need for new and improved packaged, multi-dose liquid OTC drug formulations. Such disadvantages and others inherent in the prior art are addressed by various aspects and embodiments of the subject invention.

SUMMARY OF THE INVENTION

The subject invention, in its various aspects and embodiments, relates generally to packaged over-the-counter liquid drug formulations and to multi-dose packaging systems for such formulations. The invention encompasses various embodiments and aspects, some of which are specifically described and illustrated herein.

One aspect of the invention provides for multi-dose packaged over-the-counter antitussive syrups. The packaged syrups comprise a bottle containing about 75 ml or less of a liquid formulation of dextromethorphan hydrobromide. The liquid formulation provides at least two doses of dextromethorphan hydrobromide.

Other embodiments provide such packaged syrups where the liquid formulation provides at least about 4 doses, or at least about 10 doses, or at least about 15 doses.

Still other embodiments provide such packaged syrups where the formulation is a cough syrup containing at least about 60 mg of dextromethorphan hydrobromide, or at least about 300 mg of dextromethorphan hydrobromide, or at least about 450 mg of dextromethorphan hydrobromide.

Additional embodiments provide such packaged syrups where the doses comprise from about 10 to about 30 mg of dextromethorphan hydrobromide, from about 10 to about 20 mg of dextromethorphan hydrobromide, or from about 30 mg of dextromethorphan hydrobromide. Yet other such embodiments provide doses comprising an amount of dextromethorphan hydrobromide specified by Regulatory Guidelines or by the United States FDA Final Monograph for dextromethorphan hydrobromide.

In other aspects and embodiments, the invention provides multi-dose packaged over-the-counter liquid formulations. The packaged formulations comprise a bottle having a capacity of about 100 ml or less, at least two doses of the liquid formulation carried within the bottle, a cap, a dosage cup releasably carried on the cap and a shrink wrap substantially enveloping the bottle and the dosage cup.

Other embodiments provide such packaged formulations where the packaged formulation comprises an expanded content label adhered to the shrink wrap or an expanded content label extending substantially all the way around a vertical wall of the bottle.

Still other embodiments provide such packaged formulations where the bottle has a capacity of about 75 ml or less or a capacity of about 50 ml or less.

Additional embodiments provide such packaged formulations where the formulation is a cough syrup providing at least about 2 doses of the syrup, or at least about 4 doses, or at least about 10 doses, or at least about 15 doses Yet other embodiments provide such packaged formulations where the formulation is a cough syrup that contains at least about 60 mg of dextromethorphan hydrobromide, or at least about 300 mg of dextromethorphan hydrobromide, or at least about 450 mg of dextromethorphan hydrobromide.

In other aspects and embodiments, the invention provides antitussive syrup formulations. The antitussive syrups comprise water, dextromethorphan hydrobromide in amounts from about 6 to about 25 mg/ml, and sweetener in amounts from about 200 to about 800 mg/ml.

Other embodiments provide such antitussive syrups where dextromethorphan hydrobromide is present in amounts from about 7 to about 11 mg/ml.

Additional embodiments provide such antitussive syrups where the sweetener is present in amounts from about 400 to about 700 mg/ml, where the sweetener is one or more sugars, the sweetener is one or more sugar substitutes, where the sweetener comprises one or more sugar substitutes in amounts from about 2 to about 100 mg/ml, or where the sweetener comprises one or more sugar substitutes in amounts from about 5 to about 20 mg/ml.

Still other embodiments provide such antitussive syrups where the syrup comprises an encapsulating agent or the antitussive syrups comprise propylene glycol in amounts from about 50 to about 200 mg/ml or in amounts from about 75 to 125 mg/ml. Yet other embodiments provide such antitussive syrups where the syrup comprises one or more flavorings.

Further embodiments provide such antitussive syrups where the syrup comprises a sugar, a sugar substitute, and a flavoring.

Yet other embodiments provide such antitussive syrups where the syrup comprises about 10 mg/ml of dextromethorphan hydrobromide, about 100 mg/ml of polypropylene glycol, about 650 mg/ml of high fructose corn syrup; and about 8 mg/ml of sucralose. Finally, still other aspects and embodiments of the invention will have various combinations of such features as will be apparent to workers in the art.

Thus, the present invention in its various aspects and embodiments comprises a combination of features and characteristics that are directed to overcoming various shortcomings of the prior art. The various features and characteristics described above, as well as other features and characteristics, will be readily apparent to those skilled in the art upon reading the following detailed description of the preferred embodiments and by reference to the appended drawings.

Since the description and drawings that follow are directed to particular embodiments, however, they shall not be understood as limiting the scope of the invention. They are included to provide a better understanding of the invention and the way it may be practiced. The subject invention encompasses other embodiments consistent with the claims set forth herein.

Moreover, the contents of this patent application are presented solely for the purpose of being reviewed by the United States Patent and Trademark Office or its counterparts in other countries for patentability of the claimed novel OTC drug formulations and packaged formulations. In accordance with the Federal Food, Drug, and Cosmetic Act of 1938 (FD&C), the Nutrition Labeling and Education Act of 1990 (NLEA), and the Dietary Supplement Health and Education Act of 1994 (DSHEA), it will be understood that statements made within this patent application or before other administrative agencies have not been evaluated by the FDA. Further in accordance with FD&C, NLEA, and the DSHEA, applicant is not asserting that any formulations disclosed herein are intended to diagnose, treat, prevent, mitigate or cure disease.

Figure 1:
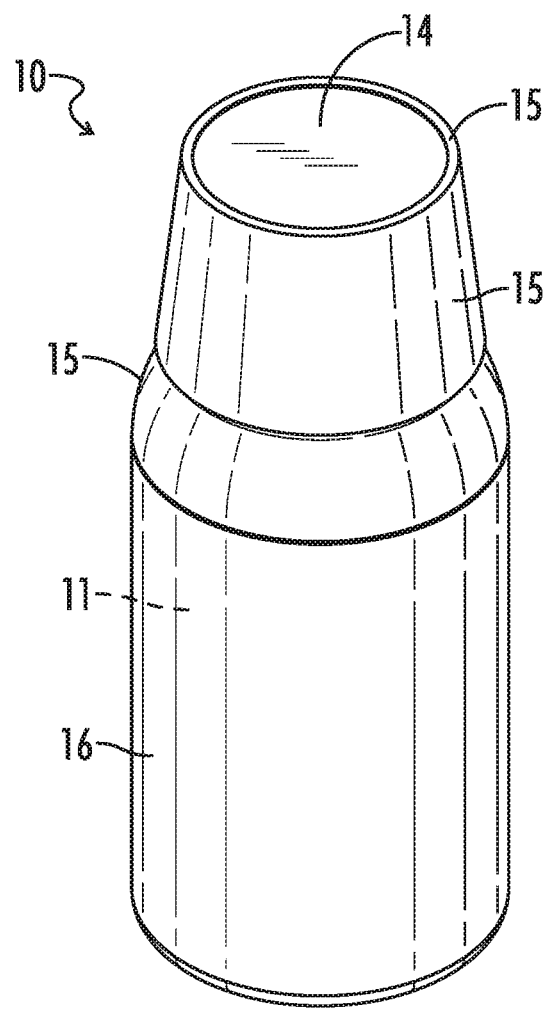
FIG. 1 is an isometric view of a first preferred embodiment 10 of the novel multi-dose packaged OTC liquid formulations, which packaged formulation 10 has a shrink wrap inner label 15 and a folded outer label 16.

In the drawings and description that follows, like parts are identified by the same reference numerals. The drawing figures are not necessarily to scale. Certain features of the embodiments may be shown exaggerated in scale or in somewhat schematic form and some details of conventional design and construction may not be shown in the interest of clarity and conciseness.

DESCRIPTION OF ILLUSTRATIVE EMBODIMENTS

The invention, in various aspects and embodiments, is directed generally to liquid OTC drug formulations and to liquid OTC drug formulations that are packaged to provide multiple doses of the formulation. Some of those embodiments are described is some detail herein. For the sake of conciseness, however, all features of an actual implementation may not be described or illustrated. In developing any actual implementation, as in any engineering or design project, numerous implementation-specific decisions must be made to achieve a developers' specific goals. Decisions usually will be made consistent within system-related and business-related constraints, and specific goals may vary from one implementation to another. Development efforts might be complex and time consuming and may involve many aspects of design, fabrication, and manufacture. Nevertheless, it should be appreciated that such development projects would be a routine effort for those of ordinary skill having the benefit of this disclosure.

Overview of Novel OTC Formulations

The novel OTC formulations are liquid formulations, often referred to as syrups. They are intended to be taken orally, and thus the base fluid is water. In general, they comprise one or more active pharmaceutical ingredients and one or more excipients. Active pharmaceutical ingredients ("APIs") are the compounds that make a drug formulation effective. They act pharmacologically to relieve symptoms or cure an underlying medical condition.

Excipients are pharmacologically inert substances that aid in delivery of the active ingredients. For example, excipients may be used to give a formulation its form, such as using cornstarch to make a tablet or sterile water to make a syrup. Other excipients may be used to control the release of the active ingredient once it is ingested. Excipients also may be used to maintain the stability of the formulation or to improve the taste or appearance of the formulation.

An OTC drug formulation, including its active ingredients and excipients, must meet various regulatory requirements in virtually all, if not all countries in order to be marketed and sold. In the United States, such regulations fall largely within 21 C.F.R. §§ 330 et seq. (Over-the Counter (OTC) Human Drugs Which are Generally Recognized as Safe and Effective and not Misbranded), and the Tentative and Final Monographs included therein. For example, the Final Monograph for DXM HBr and other oral antitussive drugs may be found at 21 C.F.R. §§ 341 et seq. Responsibility for promulgating and administering such regulations falls within the purview of the United States Food and Drug Administration (FDA). The FDA also maintains a list of approved excipients and the forms and amounts in which they may be used. In the European Union, the European Medicines Agency (EMA) assumes a similar role, and in Japan it is the Pharmaceuticals and Medical Devices Agency (PMDA).

As used herein, Regulatory Guidelines shall be understood to refer to and include the statutes and regulations governing the marketing and sale of over-the-counter drugs, including, but not limited to the allowed dosages of active ingredients for a particular indication. Regulatory Agencies shall be understood to include the FDA, EMA, PMDA, and equivalent agencies in other countries.

Active Ingredients

The active ingredient in the novel OTC drug formulations may be any active ingredient approved for use in liquid drug formulations to be sold directly to consumers under US Regulatory Guidelines or Regulatory Guidelines of another country. Preferred, active ingredients may include those listed in the FDA Final Monographs for antacids (21 C.F.R. § 331), antiflatulents (antigas) (21 C.F.R. § 332), antidiarrheal (21 C.F.R. § 335), antiemetic (21 C.F.R. § 336), nighttime sleep-aids (21 C.F.R. § 338), stimulants (21 C.F.R. § 340), cold, cough (antitussive), allergy, bronchodilator, expectorant, nasal decongestant, and antiasthmatic (21 C.F.R. § 341), analgesic-antipyretic, cardiovascular, rheumatologic (21 C.F.R. § 343).

Especially preferred active ingredients include dextromethorphan hydrobromide, either alone or with other active ingredients approved for use in combination with DXM HBr in OTC drugs.

As described further below, the active ingredient will be present in concentrated amounts allowing for the packaging of multiple doses in a small bottle. For example, DXM HBr may be added in amounts from about 6 to about 25 milligrams per milliliter (mg/ml) of formulation, preferably from about 7 to about 10 mg/ml. In other embodiments, the formulation will approach saturation when fully formulated so as to minimize the volume of formulation required to deliver a single dose of active ingredient while still passing required testing. As discussed further below, the novel, high concentration DXM HBr formulations will allow multiple doses of liquid formulation to be distributed in much smaller packaging.

It will be appreciated that the novel formulations may include more than one antitussive active ingredient. Menthol, for example, may be added to provide more immediate cough relief. They also may include other types of active ingredients. Preferred combinations will be those listed in the FDA Final Monographs. Especially preferred combinations will be those with DXM and other antitussives listed in the respective FDA Final Monograph, such as combinations with an expectorant, nasal decongestant, anesthetic/analgesic, analgesic-antipyretic, and antacid.

Preferred Excipients

Preferred embodiments of the novel OTC liquid formulations have high concentrations of DXM HBr and other active ingredients. Thus, encapsulating agents preferably will be used to facilitate dissolution of DXM HBr and other active ingredients in embodiments of the novel formulations. Sweet tasting encapsulating agents, such as propylene glycol, are preferred. Polypropylene glycol, for example, may be added in amounts from about 50 to about 200 mg/ml, or preferably, from about 75 to about 125 mg/ml.

DXM HBr and other active ingredients are known to have bitter taste that may discourage consumers from following recommended dosages at recommended intervals. That bitterness is exacerbated by increasing the concentration of DXM HBr and other active ingredients. High concentrations of DXM HBr also are known to induce nausea and vomiting. Thus, the novel OTC formulations including those having high concentrations of DXM HBr as an active ingredient preferably include high concentrations of sugar or sugar substitute sweeteners and one or more flavorings. Sweeteners preferably will be added in concentrations of from about 200 to about 800 mg/ml, preferably from about 400 to about 700 mg/ml.

Sugar and sugar substitute sweeteners are believed to provide both an antienemic effect and a taste masking effect. One or more sugars may be included in the formulation. Suitable sugars may include glucose, dextrose, disaccharides, fructose (aka levulose), galactose, high fructose corn syrup, lactose, maltose, trisaccharides, and sucrose. One or more sugar substitutes may be included in addition to or as a substitute for sugars. Sugars may be added in concentrations of from about 200 to about 800 mg/ml, preferably from about 400 to about 700 mg/ml.

Suitable sugar substitutes may include acesulfame potassium, advantame, alitame, aspartame, brazzein, curculin, dulcin, erythritol, fructooligosaccharide, glucin, glycerol, glycyrrhizin, hydrogenated starch hydrolysates, inulin, isomalt, isomaltooligosaccharide, isomaltulose, lactitol, mabinlin, maltitol, maltodextrin, mannitol, miraculin, mogroside mix, monatin, monellin, neohesperidin dihydrochalcone, neotame, osladin, pentadin, polydextrose, psicose, saccharin, salt of aspartame-acesulfame, sodium cyclamate, sorbitol, stevia, sucralose, tagatose, thaumatin, and xylitol. Sugar substitutes may be added in concentrations of from about 2 to about 100 mg/ml, preferably from about 5 to about 20 mg/ml.

One or more flavorings also may be included to mask the taste of DXM and other active ingredients. Suitable flavorings may include artificial flavors, artificial vanilla, dimethyl anthranilate, eculyptol, menthol, methyl anthranilate, methyl salicylate, natural flavors, peppermint, thymol, various fruit flavors, and culinary herbs and spices. Flavorings typically will be added to taste.

Other Excipients

Preferred embodiments also may include other excipients, such as extenders, diluents, wetting agents, solvents, emulsifiers, preservatives, absorption enhancers, sustained-release matrices, and coloring agents. Preferred excipients will be those listed for use in OTC drug formulations.

Novel Multi-Dose Packaged OTC Formulations

Preferred embodiments of the invention will provide multiple doses of a liquid DXM HBr or other OTC formulation in a relatively small bottle. For example, a preferred multi-dose packaged OTC formulation 10 is shown in FIGS. 1-5. As shown therein, packaged formulation 10 generally includes a bottle 11, a seal 12, a cap 13, a dosage cup 14, an inner shrink wrap 15, and an outer expanded content label 16. Bottle 11 and cap 13 may be of any conventional design and shape suitable for holding liquids and many suitable bottles and caps are available commercially.

Bottle 11, for example, is a "Boston round" design. It has a generally cylindrical shape with relatively long vertical walls. The top of bottle 11 tapers rapidly into a relatively flat shoulder surrounding a relatively small neck and opening. Bottle 11 may be made from conventional material by conventional methods. Preferably, however, bottle 11 is made from polymers, such as polypropylene, high-density and other polyethylenes, and polyethylene terephthalate, by blow molding. As noted, the shape of bottle 11 and cap 13 is not critical. Importantly, however, bottle 11 is relatively small, preferably having a capacity of less than 100 ml, and more preferably, less than about 75 or 50 ml.

The opening of bottle 11 preferably is sealed with seal 12. Seal 12 not only helps to preserve the formulation, but it can provide an indicator that the product has not been tampered with or adulterated. Seal 12 may be fabricated from conventional materials and applied by conventional methods. For example, a 'lift-n-peel" induction seal may be used and sealed over the opening of bottle 11 by induction heating. Lift-n-peel liners provide a tab by which a consumer can peel the seal off.

The neck of bottle 11 and cap 13 may incorporate any conventional design that allows cap 13 to provide a liquid-tight closure for bottle 11, such as a threaded cap. Preferably, however, cap 13 is a child resistant cap. Many conventional child resistant caps are known and may be used, such as a "push and turn" cap. Typically, such caps are molded from plastics such as polypropylene or polyethylene terephthalate and are widely available. Cap 13 also may incorporate a liner to aid in sealing the opening.

Dosage cup 14, as its name implies, is a small open cup that is primarily designed to allow a consumer to measure a recommended dose of the liquid formulation. Preferably it is fabricated from a clear plastic, such as polypropylene, and is embossed with markings indicating the recommended dosage line. A consumer may more accurately confirm that the amount of formulation in the cup matches the recommended dose.

The length of dosage cup 14 is not particularly critical so long as it provides sufficient depth to accommodate the volume of a dose. The inner diameter of dosage cup 14, however, is preferably sized and configured to fit securely over cap 13. Many conventional designs are known and may be used. For example, dosage cup 14 may be provided with interior vertical ribs. When dosage cup 14 is placed over cap 13 the ribs will provide a friction fit. Ribs also may be designed to clip on to the underside of cap 13. In any event, dosage cup 14 preferably is releasably secured to cap 13, minimizing the likelihood of it being misplaced or lost by a consumer, but ensuring that it is readily available for use.

Typically, bottle 11 will be filled to slightly less than capacity to avoid spillage during packaging. Thus, bottle 11 preferably will be filled to less than about 75 ml, and preferably less than about 50 ml or less than about 40 ml. Preferably, the amount of syrup contained in packaged formulation 10 will be coordinated with the concentration of DXM HBr to provide a specific number of recommended doses.

The FDA Final Monograph lists the dosages under which DXM HBr OTC drugs may be marketed. For adults and children 12 years of age or older the oral dosage is 10 to 20 mg every 4 hours or 30 mg every 6 to 8 hours, not to exceed 120 mg in 24 hours, or as directed by a doctor. For children 6 to under 12 years of age the oral dosage is 12.5 mg every 4 hours, not to exceed 75 mg in 24 hours, or as directed by a doctor. OTC formulations containing DXM HBr are not to be used for children under 6 years of age except as recommended by a doctor.

Thus, when present in amounts of about 10 mg/ml, for example, a single adult, 6 to 8-hour dose of the formulation will be 3 ml, and 15 doses will be 45 ml. Dosage cup 14 in this example would provide a 3 ml indicator line. If the formulation was labeled for recommended adult, 4-hour doses of 20 mg, dosage cup would provide a ml indicator line. Fifteen doses could be provided by 30 ml of formulation, or 30 doses could be provided by 60 ml of formulation. In general, therefore, the bottle will be filled with sufficient formulation to provide at least about 60 mg of DXM HBr, or at least about 120 mg of DXM HBr, or at least about 300 mg of DXM HBr, or at least about 450 mg of DXM HBr. The formulation will be packed to provide at least 2 doses. More commonly, it may be provided with at least about 4 doses, or at least about 10 doses, or at least about 15 doses.

Shrink wrap 15 may be used to secure dosage cup 14 during packing, shipment, and sale. It also may provide an indication of tampering or adulteration. Shrink wrap 15 may be any suitable conventional shrink wrap, such as those made from polyvinyl chloride and polyolefins. A relatively narrow band may be provided and will be sufficient to secure dosage cup 14. Preferably, however, shrink wrap 15 will substantially envelope the assembly of bottle 11, cap 13, and dosage cup 14. For example, as may be seen in FIGS. 1-2, shrink wrap 15 extends from partially under the bottom of bottle 11 all the way up and partially over the bottom of dosage cup 14. Dosage cup 14 is secured to bottle 11 and cap 13, and as discussed further below, shrink wrap 15 can provide a substrate on which branding and other messages may be imprinted. Perforations or other weakened areas may be provided in shrink wrap 15 to allow a consumer to easily remove dosage cup 14. Preferably, especially if shrink wrap 15 is imprinted with branding or other messages, the perforations will allow dosage cup 14 to be removed while leaving most of shrink wrap 15 on bottle 11.

Figure 2:
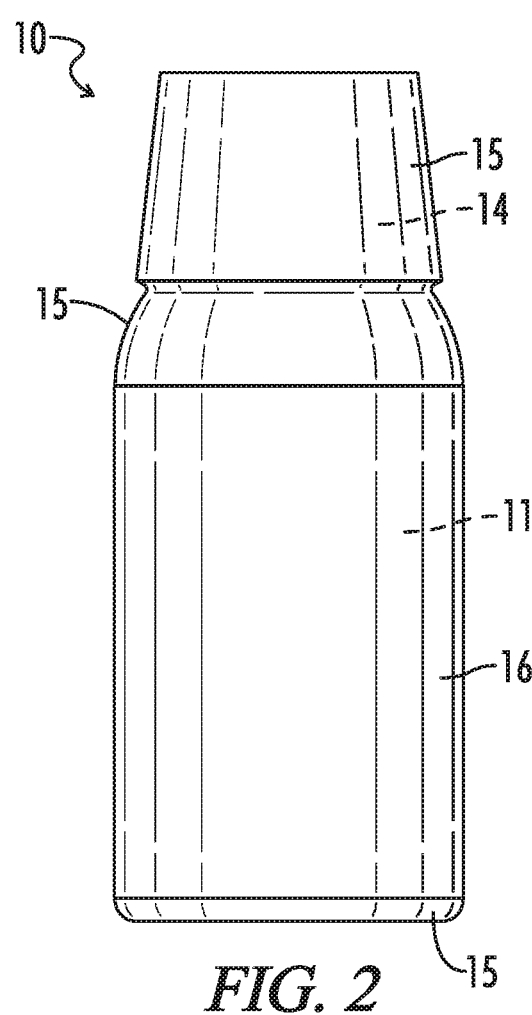
FIG. 2 is an elevational view of packaged formulation 10 shown in FIG. 1.

Expanded content label 16 is affixed to shrink wrap 15. Many conventional expanded content labels are available commercially and may be used. Such labels have multiple plies which provide a substrate on which branding and other messages may be imprinted. Label 16, for example, is a continuous web having a single lateral fold. The back of the label is provided with a relatively strong adhesive such that label 16 is self-adhering. The folded portions of label 16 are lightly adhered so that they may be peeled apart to expose their inner sides. Preferably, as shown in FIGS. 1-2, label 16, when folded and applied to bottle 11 extends substantially completely around bottle 11. Doing so will avoid the need to register label 16 with indicia imprinted on shrink wrap 15. Other types of expanded content labels may be used if desired. For example, other expanded content labels have one or more webs that are joined or folded to form a booklet.

It will be appreciated, therefore, that embodiments of the novel packaged OTC formulations have significant advantages over the prior art. By packaging a highly concentrated liquid formulation in a relatively small bottle, the packaged formulation may contain multiple doses yet may be easily accommodated on a retailer's shelf. As noted previously, that is particularly critical for retailers, such as convenience stores, where shelf space in severely constrained.

Moreover, while other forms of labeling may be used if desired, by providing a combination of a full shrink wrap and an expanded content label, such as shrink wrap 15 and label 16, the packaging may be provided with sufficient space to comply with regulatory labeling requirements while allowing space for branding and other optional messages and bar coding. It may not be necessary to distribute individual products in additional packaging, such as individual paperboard boxes.

It will be appreciated that various functions and mechanisms are ascribed to each component of the novel formulations and packaged formulations and to their effect on the overall properties thereof. While such explanations are believed to be accurate, and are believed to provide useful guidance in making and using various embodiments of the novel formulations and packaged formulations, it will be understood that the invention is not limited thereby. The economics and characteristics of a particular embodiment also may render it more suitable for particular purposes. One embodiment may be well suited for one application and unsuited for another. Thus, general statements should be taken as such, and not as definitive, immutable principles.

EXAMPLES

The invention and its advantages may be further understood by reference to the following examples. It will be appreciated, however, that the invention is not limited thereto.

Example 1—Prior Art

A sample of a Robitussin Adult Peak Cold liquid product was purchased at a convenience store. The product was labeled as Cough+Chest Congestion DM. The syrup was packaged in a bottle containing 4 ounces (118 ml) of syrup. The syrup contained 2 mg/ml of DXM HBr and 20 mg/ml guaifenesin (an expectorant). The recommended adult dose was 20 mg, and thus the size of the dose was 10 ml. The bottle contained approximately 11 to 12 doses.

The bottle was packaged in a paperboard box measuring approximately 2" wide, 2" deep, and 5" tall. It is estimated that a dozen such products will occupy 48 square inches of shelf space. Stacked 3-deep, a dozen products will require approximately 8" of shelf frontage.

Example 2

A novel liquid DXM HBR formulation was prepared having the components set forth in Table 1 below.

TABLE 1

| Component | Concentration (mg/ml) |
|---|---|
| Sodium Benzoate | 1 |
| Grape Flavoring (Methyl Anthranilate) | 2 |
| Phosphoric acid | 4.9 |
| Sucralose | 8 |
| DXM HBR | 10 |
| Propylene Glycol | 100 |
| Water | 435 |
| High Fructose Corn Syrup 55 | 650 |

High fructose corn syrup was added to a first tank containing a portion of the indicated water and heated to 40° C. Approximately half of the water was heated in a second tank to 40° C. The sodium benzoate and sucralose were added to Tank 2 and stirred until dissolved. The heated contents of Tank 2 were transferred to Tank 1. Tank 2 was rinsed twice, each rinse being approximately 5% of the indicated water, and the rinse added to Tank 1. Propylene glycol was added to a third tank and heated to 40° C. DXM HBR was added to the heated propylene glycol and stirred until dissolved. Grape flavoring was added to Tank 3 and stirred until dissolved. Phosphoric acid was added to Tank 3 and stirred until homogeneity. The contents of Tank 3 were added to Tank 1. Tank 3 was rinsed twice, each rinse being approximately 5% of the indicated water. The remaining water was added to Tank 1 and the formulation was stirred to homogeneity.

Two milliliters of the resulting formulation contain 20 mg DXM HBr, an adult, 4-hour dosage indicated in the Final Monograph for antitussives. Three milliliters of the resulting formulation contain 30 mg of DXM HBR, a recommended adult, 6 to 8-hour dosage. Thus, it is believed that a 3 ml dose of the formulation will be effective in suppressing coughs in adults for a period of 6-8 hours.

The formulation was tasted and found to have an acceptable taste with no bitterness.

Example 3

Figure 3:
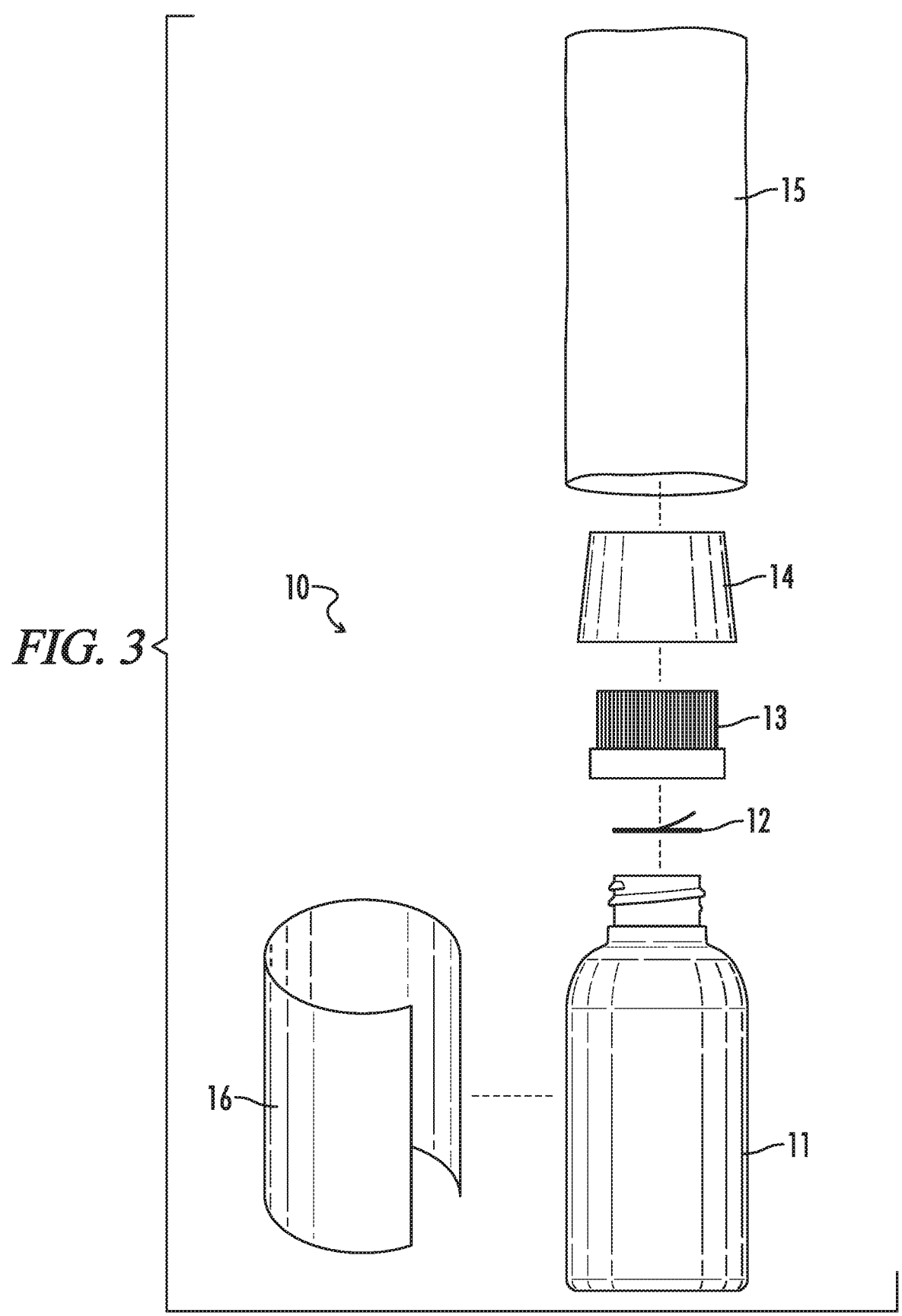
FIG. 3 is an exploded view of packaged formulation 10 showing the various components thereof.

The formulation prepared according to Example 2 was packaged in packaging substantially identical to packaged formulation 10 shown in FIGS. 1-3. The novel packaged formulation 10 was approximately 3.5" high and had a primary diameter of approximately 1.375". The bottle 11 had a capacity of 60 ml and was filled with 45 ml of the formulation. The packaged formulation 10 was labeled for use by adults and recommended a dosage of 30 ml. Thus, the package formulation 10 provided 15 of the recommended adult doses.

Figure 4:
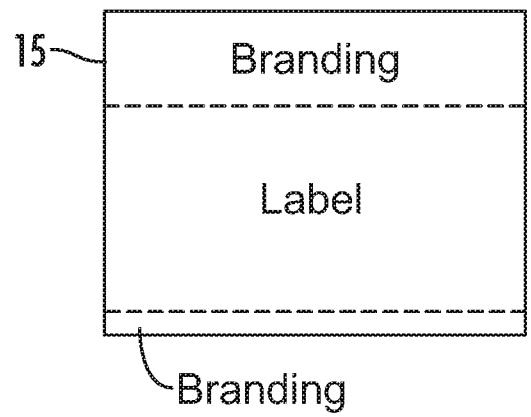
FIG. 4 is a plan view of unwrapped inner shrink wrap 15 of packaged formulation 10.
Figure 5A:
FIG. 5A is a plan view of unrolled folded outer label 16 of packaged formulation 10 showing the outer fold thereof.
Figure 5B:
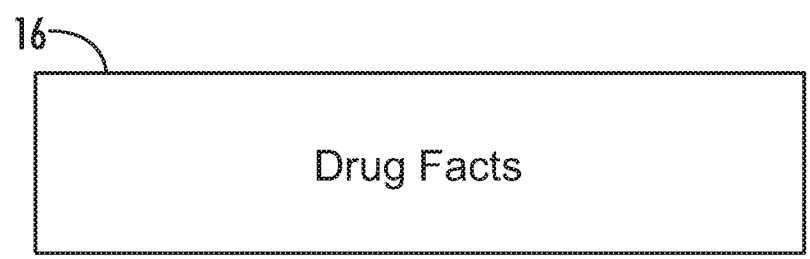
FIG. 5B is a plan view of unfolded outer label 16 of packaged formulation 10 showing the inner fold thereof.

Shrink wrap 15 and label 16 are shown at approximately half size in FIGS. 4-5. Label 16 when folded as shown in FIG. 5A is approximately 1.875"×4.5" and extends substantially all the way around bottle 11. Label 16 unfolds, as shown in FIG. 5B, to approximately 8.125". Approximately 1.375" of the right end of the folded label 16 was devoted to drug facts and labeling information required by the Final Monograph as shown in FIG. 5A. All of the interior of folded label 16 was devoted to drug facts as shown in FIG. 5B. All labeling required by the Final Monograph was imprinted in a font no less than 6 points as required by the Final Monograph.

Notwithstanding the extensive labeling requirements imposed by the Final Monograph, it was found that packaged formulation 10 still provided ample space for branding and other optional messages. Approximately 3.125" of the left end of folded label 16 may be used for branding, a total area of approximately 6 in$^2$. In addition, as shown in FIG. 4, approximately 1.25" of the upper portion of shrink wrap 15 and a strip at the bottom of shrink wrap 15 are available for branding messages. Those areas were sufficient to provide packaged formulation 10 with distinctive and readily observable branding.

Importantly, packaged formulation 10 provided space for all required labeling and for branding and other optional messages without the need to package formulation 10 in any additional individual packaging, such as a paperboard box.

Example 4

Novel packaged formulations 10 prepared according to Example 3 were packaged in a paperboard shipping-display box. The box had a fold and tuck top that provided a billboard for branding messages. The box was approximately 5.525" wide, 4.25" deep, and 3.5" high and held 12 packaged formulations 10. The box negligibly increased the footprint of the formulations 10 contained therein and had a footprint of only about 23.5 square inches. The box occupies approximately 5.5" of shelf frontage.

In contrast, the equivalent number of Robitussin products of Example 1 have a footprint of approximately 48 square inches on a shelf and take up 8 inches of frontage. It is expected that twice as many units of novel formulations 10 can be provided in about 70% of shelf frontage as required for the Robitussin product.

Moreover, each novel formulation 10 will provide the consumer with 15 adult, 6 to 8-hour doses (30 mg/dose). Novel formulation 10 also could be labeled for adult 4-hour doses, for example 20 mg, and provide 22.5 doses. The Robitussin product of Example 1 was labeled for 20 mg doses, and thus provides only 11 to 12 doses—about half the 20 mg doses that would be provided by novel formulation 10. Similarly, if the Robitussin product was labeled for 30 mg doses, it would contain less than 8 doses. Novel formulation 10 contains twice as many 30 mg doses: 15.

It is believed that the examples as a whole show that the novel packaged OTC drug formulations can provide surprising and useful advantages in distributing the formulations through previously underpenetrated markets. The novel packaged OTC formulations can provide an equivalent or greater number of doses of a liquid formulation, but occupy significantly less shelf space. Such qualities make the novel packaged OTC formulations much more attractive to convenience stores and other small retail outlets.

While this invention has been disclosed and discussed primarily in terms of specific embodiments thereof, it is not intended to be limited thereto. Other modifications and embodiments will be apparent to the worker in the art.

What is claimed is:

1. An antitussive syrup formulation, said antitussive syrup comprising:
   (a) water;
   (b) dextromethorphan hydrobromide, wherein said dextromethorphan hydrobromide is not complexed with sustained-release matrices and is dissolved in said formulation in amounts from about 6 to about 25 mg/ml;

(c) sweetener, said sweetener being one or more sweeteners selected from the group consisting of sugars, said sugars being present in amounts from about 200 to about 800 mg/ml, and sugar substitutes, said sugar substitutes being present in amounts from about 2 to about 100 mg/ml; and (d) wherein said syrup is an aqueous syrup and is not an extended-release formulation providing extended release of protonated dextromethorphan.

2. The antitussive syrup of claim 1, wherein dextromethorphan hydrobromide is present in amounts from about 7 to about 11 mg/ml.

3. The antitussive syrup of claim 1, wherein said sugars are present in amounts from about 400 to about 700 mg/ml.

4. The antitussive syrup of claim 1, wherein said sweetener is one or more sugars.

5. The antitussive syrup of claim 1, wherein said sweetener is one or more sugar substitutes.

6. The antitussive syrup of claim 1, wherein said sugar substitutes are present in amounts from about 5 to about 20 mg/ml.

7. The antitussive syrup of claim 1, wherein said syrup comprises an encapsulating agent.

8. The antitussive syrup of claim 1, wherein said syrup comprises propylene glycol in amounts from about 50 to about 200 mg/ml.

9. The antitussive syrup of claim 1, wherein said syrup comprises one or more flavorings.

10. The antitussive syrup of claim 1, wherein said syrup comprises propylene glycol in amounts from about 75 to about 125 mg/ml.

11. The antitussive syrup of claim 1, wherein said syrup comprises protonated dextromethorphan in molar amounts substantially equal to molar amounts of dextromethorphan hydrobromide added to the syrup.

* * * * *